(12) United States Patent
Hart et al.

(10) Patent No.: US 8,961,493 B2
(45) Date of Patent: Feb. 24, 2015

(54) SURGICAL ACCESS APPARATUS AND METHOD

(75) Inventors: Charles C. Hart, Summerville, SC (US); John R. Brustad, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 822 days.

(21) Appl. No.: 13/078,750

(22) Filed: Apr. 1, 2011

(65) Prior Publication Data

US 2011/0196307 A1     Aug. 11, 2011

Related U.S. Application Data

(63) Continuation of application No. 11/383,927, filed on May 17, 2006, now Pat. No. 7,942,862, which is a continuation of application No. 10/379,461, filed on Mar. 3, 2003, now Pat. No. 7,070,586, which is a continuation-in-part of application No. 10/346,846, filed on Jan. 17, 2003, now Pat. No. 6,887,194.

(51) Int. Cl.
  *A61M 31/00*   (2006.01)
  *A61M 5/178*   (2006.01)
  (Continued)

(52) U.S. Cl.
  CPC ......... *A61B 17/3421* (2013.01); *A61B 17/3417* (2013.01); *A61M 25/04* (2013.01); *A61B 1/3132* (2013.01); *A61B 17/3474* (2013.01); *A61B 19/5202* (2013.01); *A61B 2017/00685* (2013.01); *A61B 2017/320044* (2013.01); *A61B 2017/3405* (2013.01); *A61B 2017/3484* (2013.01); *A61B 2017/349* (2013.01); *A61B 2019/481* (2013.01); *A61B 2019/5231* (2013.01); *A61M 25/02* (2013.01); *A61M 2025/0286* (2013.01)

USPC ......... 604/506; 604/164.04; 604/23; 606/108

(58) Field of Classification Search
None
See application file for complete search history.

(56) References Cited

U.S. PATENT DOCUMENTS

| | | |
|---|---|---|
| 4,254,762 A | 3/1981 | Yoon |
| 4,762,130 A | 8/1988 | Fogarty et al. |

(Continued)

FOREIGN PATENT DOCUMENTS

| | | |
|---|---|---|
| DE | 295 21 431 U1 | 4/1997 |
| WO | WO 96/01132 | 1/1996 |

OTHER PUBLICATIONS

Co-Pending U.S. Appl. No. 11/009,440, filed Dec. 9, 2004. Title: Insufflation Gas Warmer and Humidifier.

(Continued)

*Primary Examiner* — Dianne Dornbusch
*Assistant Examiner* — Michael Mendoza
(74) *Attorney, Agent, or Firm* — Rimas T. Lukas

(57) ABSTRACT

A trocar system for providing access across a body wall includes a trocar and an anchor provided in the form of a first helix. The anchor is adapted for placement in an operative position wherein the anchor extends at least partially through the body wall. A second helix formed on the trocar is size and configured to engage the first helix of the anchor so that rotation of the trocar relative to the anchor moves the second helix along the first helix. In this manner, the trocar is drawn into the anchor as it moves into the body wall. A proximal force applied to the anchor resists tenting of the abdominal wall. The anchor also holds the layers of the body wall together thereby resisting peritoneal separation.

16 Claims, 19 Drawing Sheets

(51) Int. Cl.
*A61M 37/00* (2006.01)
*A61F 11/00* (2006.01)
*A61B 17/34* (2006.01)
*A61M 25/04* (2006.01)
*A61B 1/313* (2006.01)
*A61B 19/00* (2006.01)
*A61B 17/00* (2006.01)
*A61B 17/32* (2006.01)
*A61M 25/02* (2006.01)

(56) References Cited

U.S. PATENT DOCUMENTS

| | | | |
|---|---|---|---|
| 4,878,492 A * | 11/1989 | Sinofsky et al. | 606/7 |
| 5,334,150 A | 8/1994 | Kaali | |
| 5,407,427 A * | 4/1995 | Zhu et al. | 604/26 |
| 5,443,484 A | 8/1995 | Kirsch et al. | |
| 5,577,993 A | 11/1996 | Zhu et al. | |
| 5,630,805 A | 5/1997 | Ternamian | |
| 5,658,306 A * | 8/1997 | Kieturakis et al. | 606/184 |
| 5,685,820 A | 11/1997 | Riek et al. | |
| 5,695,462 A | 12/1997 | Sutcu et al. | |
| 5,738,628 A | 4/1998 | Sierocuk et al. | |
| 5,842,971 A | 12/1998 | Yoon | |
| 5,941,852 A | 8/1999 | Dunlap et al. | |
| 5,957,888 A | 9/1999 | Hinchliffe | |
| 5,976,079 A | 11/1999 | Volz et al. | |
| 6,001,084 A | 12/1999 | Riek et al. | |
| 6,068,637 A | 5/2000 | Popov et al. | |
| 6,468,228 B1 | 10/2002 | Topel et al. | |
| 6,471,638 B1 * | 10/2002 | Chang et al. | 600/114 |
| 6,508,759 B1 | 1/2003 | Taylor et al. | |
| 2005/0107803 A1 | 5/2005 | Guanche | |

OTHER PUBLICATIONS

Co-Pending U.S. Appl. No. 11/680,835, filed Mar. 1, 2007. Title: Gas Insufflation and Suction/Irrigation Tubing.

Co-Pending U.S. Appl. No. 11/868,901, filed Oct. 8, 2007. Title: Method for Manufacturing High Flow Insufflation Needle Stylet.

Co-Pending U.S. Appl. No. 11/062,022, filed Feb. 18, 2005. Title: Surgical Access Apparatus and Method.

Co-Pending U.S. Appl. No. 11/383,927, filed May 17, 2006 Title: Surgical Access Apparatus and Method.

European Patent Office, Supplementary Partial European Search Report for European Patent Application No. EP 04 71 2378 and International Application No. PCT/US2004/004883, dated May 9, 2008.

European Patent Office, Supplementary Partial European Search Report for European Patent Application No. EP 04 70 1731 based on International Application No. PCT/US2004/000695, dated Apr. 11, 2007.

* cited by examiner

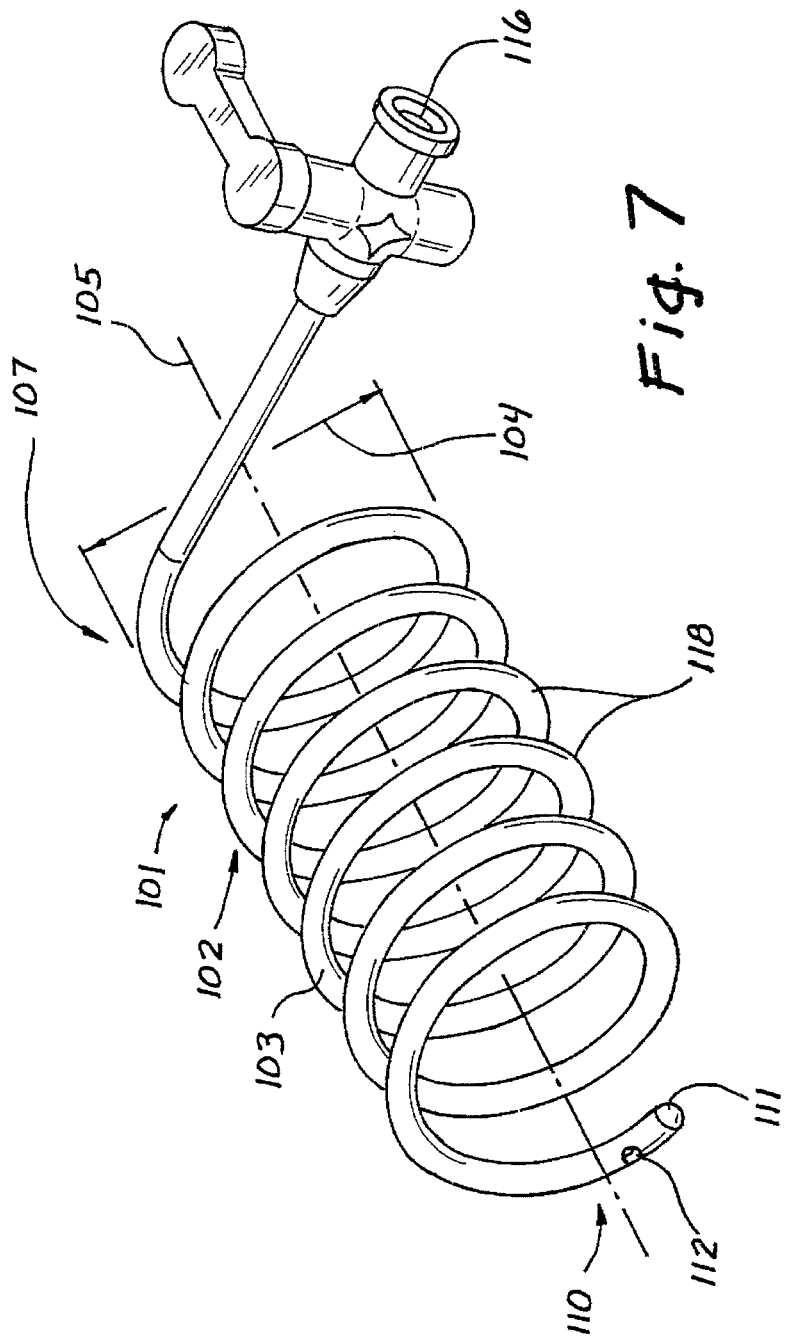

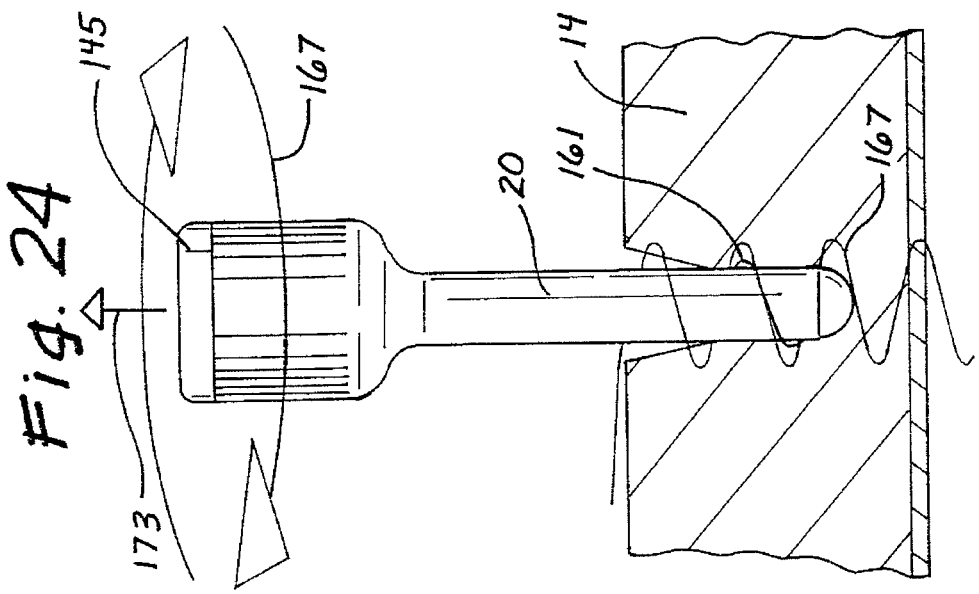
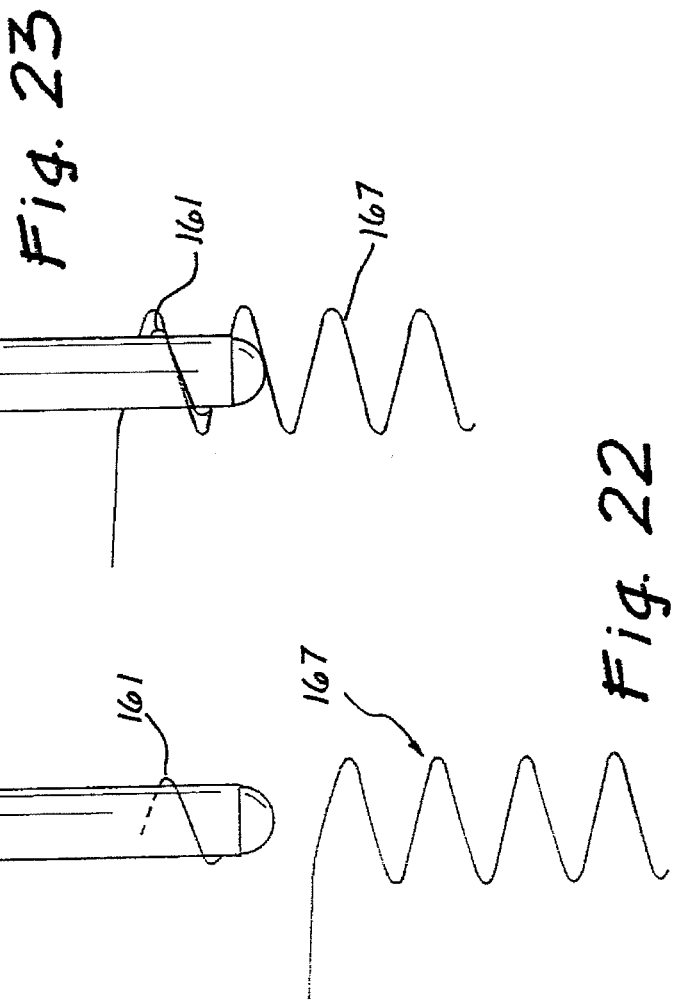

SURGICAL ACCESS APPARATUS AND METHOD

CROSS REFERENCE TO RELATED APPLICATIONS

This application is a continuation of U.S. patent application Ser. No. 11/383,927, filed May 17, 2006, which is a continuation of U.S. patent application Ser. No. 10/379,461, filed Mar. 3, 2003 and issued as U.S. Pat. No. 7,070,586 on Jul. 4, 2006, which is a continuation-in-part of U.S. patent application Ser. No. 10/346,846 filed Jan. 17, 2003 and issued as U.S. Pat. No. 6,887,194 on May 3, 2005, the disclosures of which are all hereby incorporated by reference as if each is set forth in full herein.

BACKGROUND OF THE INVENTION

1. Field of the Invention

This invention relates generally to surgical access devices and more specifically to trocars and insufflation devices used in laparoscopic surgery.

2. Discussion of Related Art

Abdominal inflation is a critical component of Laparoscopic Surgery. The most common method to achieve inflation, more commonly referred to as insufflation, is to pass a sharp needle through the abdominal wall and into the inner abdominal region, and then inject a gas through the needle and into the region thereby creating an enlarged or ballooned cavity to accommodate a laparoscopic procedure. Unfortunately, insertion of the needle has been required without any visual aid to facilitate location of the sharp needlepoint. In order to reduce the probability of inadvertent penetration of delicate internal organs in this "blind" procedure, the sharp insufflation needle has been provided with a spring-loaded and retractable safety mechanism.

The safety mechanisms associated with most insufflation needles consist of a blunt or rounded member disposed within the lumen of the needle, and biased by a spring to an extended position beyond the needle tip. This spring must be responsive to the insertion pressure during placement of the needle but must be capable of immediately moving forward when that pressure is relieved. This is highly mechanical event and at best, offers a less than optimal arrangement.

In order to make the insertion of sharp needles into the abdominal region safer, a common practice has developed where the needle is inserted at an angle to the tissue plane. This of course requires that the needle traverse a greater distance through the abdominal tissue, so the maximum angle is always limited by the length of the needle.

Notwithstanding these attempts to reduce the probability and severity of an adverse consequence, many inadvertent injuries continue to result from the blind insertion of insufflation needles.

SUMMARY OF THE INVENTION

In a preferred embodiment of the present device, a length of hollow tubing, configured as a helix, is provided with a closed and rounded distal end. At least one distal side opening allows insufflation gas to exit the spiral tube at the distal end. The proximal end of the spiral tube is fitted with a connecting hub and a valve for connection to a gas supply. In operation, the spiral tube is inserted into a small skin incision and subsequently rotated to separate or part abdominal tissue until the distal end emerges from the abdominal wall and into the abdominal region. A significant characteristic of the spiral tube is that its distal tip emerges nearly parallel to the plane of the inner surface of the abdominal wall and the adjacent internal organs. With this orientation, the blunt distal end of the device presents no danger to these delicate internal structures.

In one aspect, a laparoscopic insufflation needle is adapted for movement across an abdominal wall of a patient to insufflate an abdominal region of the patient, the needle comprises an elongate tube having an inflation channel extending between a proximal end and a distal end. The tube is adapted at the proximal end for connection to a source of fluid under pressure, and is adapted at its distal end to expel the fluid under pressure to insufflate the abdominal region of the patient. An optical element can be disposed at the distal end of the elongate tube to facilitate visualization of the abdominal wall and the abdominal region of the patient.

In another aspect, an insufflation needle is adapted for movement across an abdominal wall and into an abdominal region of a patient. The needle includes an elongate tube for insufflating the abdominal region with a fluid under pressure. The tube is configured to provide a mechanical advantage when moved across the abdominal wall.

In another aspect, the insufflation needle includes an elongate tube for insufflating the abdominal region with a fluid under pressure. The elongate tube at its distal end is angled relative to the proximal end of the tube to produce an exit angle with an interior surface of the abdominal wall. This exit angle is in a range of less than about 40 degrees in order to inhibit penetration of interior organs of the patient.

In another aspect, the elongate tube of the insufflation needle has a distal end with a distal tip that is free of sharp edges to inhibit cutting the abdominal wall during penetration of the abdominal wall, and to inhibit cutting the interior organs following penetration of the abdominal wall.

An associated method for accessing an abdominal region of the patient by crossing an abdominal wall of the patient, includes the steps of providing an insufflation needle in the configuration of a tube, and turning the tube to facilitate the crossing of the abdominal wall with the insufflation needle.

In another method, an access device is used to create an abdominal cavity in an abdominal region containing interior organs of the patient. The method includes the steps of providing an elongate shaft having an axis extending between a proximal end and a distal end, and moving the shaft across the abdominal wall to place the distal end of the shaft in the abdominal region. Following this placement, the elongate shaft can be pulled to move the abdominal wall away from the interior organs and to create the abdominal cavity around the interior organs in the abdominal region.

In a further aspect, a surgical device is adapted to provide access across an abdominal wall and into an abdominal region of a patient. The device includes a trocar with a blunt tip obturator and a cannula. A shaft with a proximal end and a distal end forms a coil having a coil axis, the coil being adapted to facilitate rotational movement of the shaft across the abdominal wall. The proximal end of the shaft is coupled to the trocar so that movement by the shaft across the abdominal wall is accompanied by movement of the trocar into the abdominal wall.

In an associated method, a trocar is placed across an abdominal wall of a patient by providing a shaft in the form of a coil having a proximal end and a distal end. The proximal end of the coil is coupled to the trocar so that screwing the coil into the abdominal wall moves the trocar with the shaft into the abdominal wall with a mechanical advantage which is dependent upon the configuration of the coil.

In a further aspect, an anchor is adapted for use with a trocar having a cannula configured for placement in an operative position across an abdominal wall. The anchor includes a coiled structural element which extends outwardly of the cannula. This structural element has properties for engaging the abdominal wall at a location spaced from the cannula to inhibit withdrawal of the cannula from its operative position.

Alternatively, the trocar can be removably coupled to the anchor by an external thread or helix which engages the coiled anchor. By screwing the trocar into the anchor, a proximally directed force can be applied to the trocar to elevate the abdominal wall while penetrating the abdominal wall.

These and other features and advantages of the invention will be better understood with reference to certain preferred embodiments and their associated drawings.

DESCRIPTION OF THE DRAWINGS

FIG. 7 is a perspective view of one embodiment of the present insufflation device;

FIGS. 20-26 illustrate a further embodiment of the invention;

FIG. 20 is a perspective view of the insufflation device or anchor associated with this embodiment;

FIG. 21 is an assembled view showing an obturator inserted into a cannula having an external helix;

FIG. 22 is a side elevation view of the trocar and anchor of this embodiment;

FIG. 23 is a side elevation view showing engagement of the anchor by the trocar;

FIG. 24 is a side elevation view of the trocar and anchor operably disposed in a perpendicular relationship with a body wall;

FIG. 25 is a side elevation view of the trocar and anchor operably disposed in an oblique relationship with the body wall; and FIG. 26 illustrates proximal external forces applied to the trocar to elevate the abdominal wall, while distal internal forces are applied to the trocar to penetrate the abdominal wall.

DESCRIPTION OF PREFERRED EMBODIMENTS AND BEST MODE OF THE INVENTION

Figure 1:
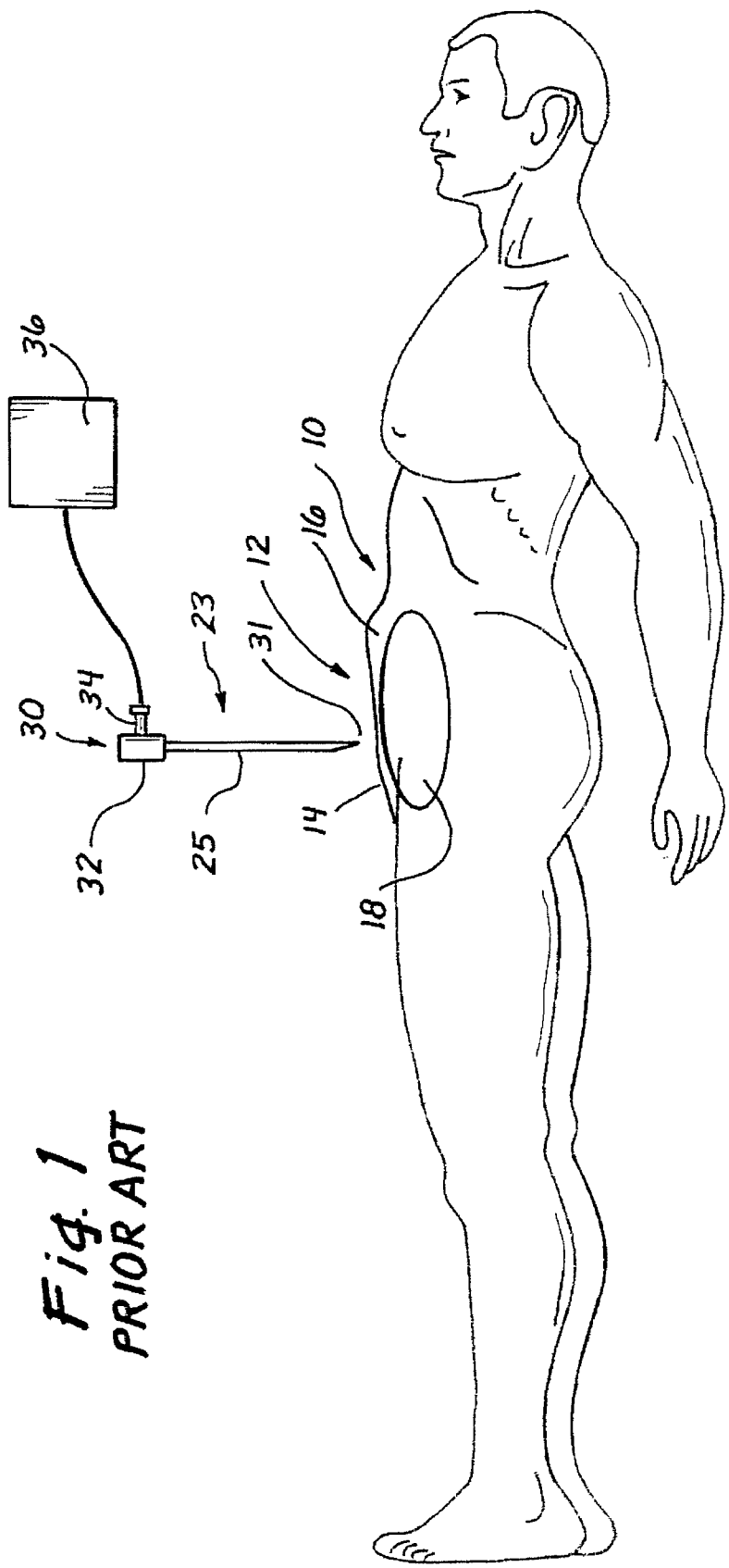
FIG. 1 is a side view of a patient in a prone position and prepared for laparoscopic surgery.
Figure 2:
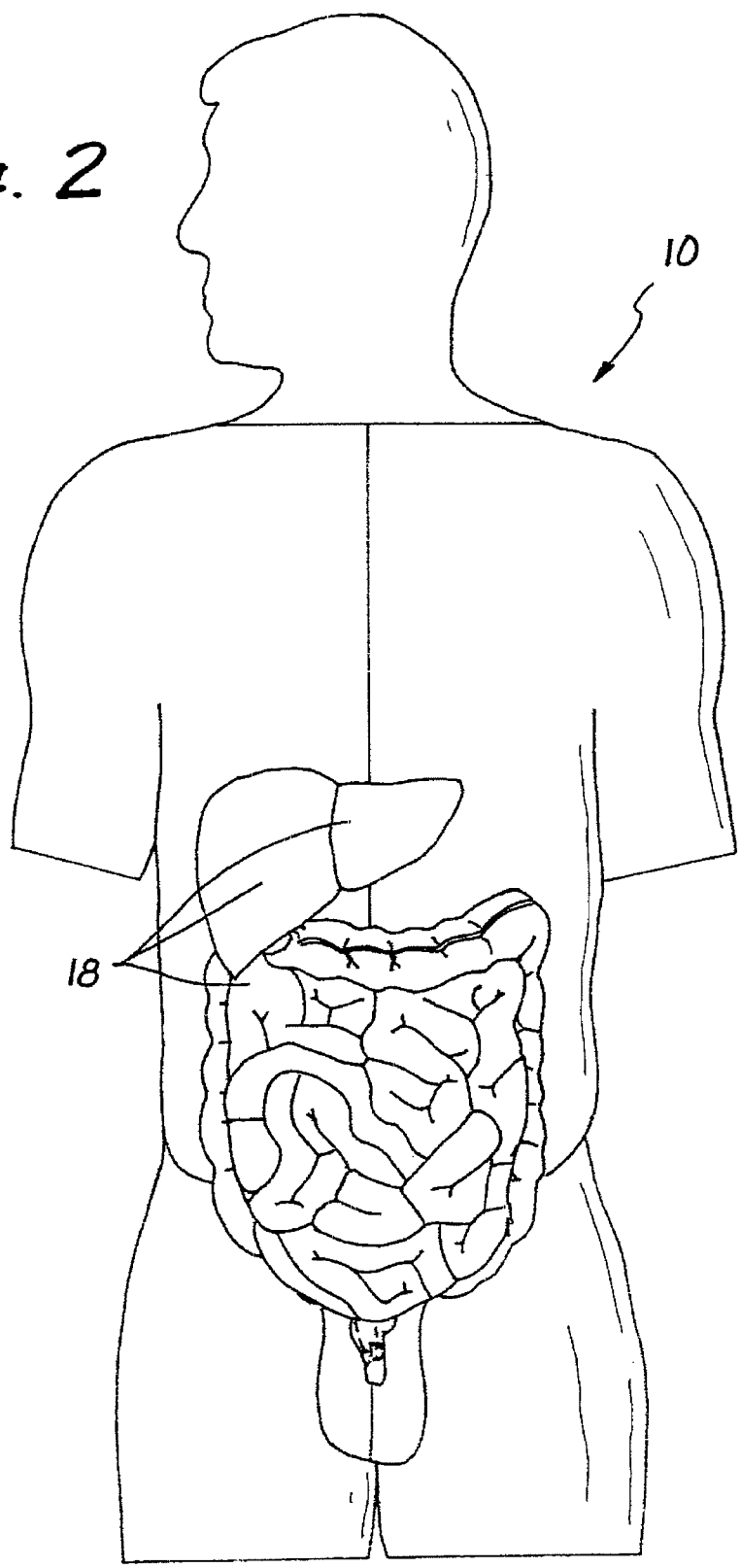
FIG. 2 is a top plan view showing organs internal to an abdominal region of the patient.

A patient is illustrated in FIG. 1 and designated generally by the reference numeral 10. The patient 10 is shown in a prone position with his abdomen 12 facing upwardly as he is readied for laparoscopic surgery. In this process, minimally invasive surgery is undertaken through an abdominal wall 14 and within an abdominal region 16 of the patient. This laparoscopic surgery commonly involves internal organs 18 as best illustrated in FIG. 2. Rather than accessing these internal organs 18 through a large opening in the abdominal wall 14, laparoscopic surgery calls for minimal invasion of the abdominal wall 14 through tubular access devices, commonly referred to as trocars. These trocars are designated by the reference numeral 20 in FIG. 3.

The trocars 20 are placed through small openings in the abdominal wall to provide access for visualization and surgical instruments. They are commonly provided with sharp points which although facilitating puncture of the abdominal wall, can be particularly threatening to the internal organs 18 which initially are in close proximity to the abdominal wall.

Figure 3:
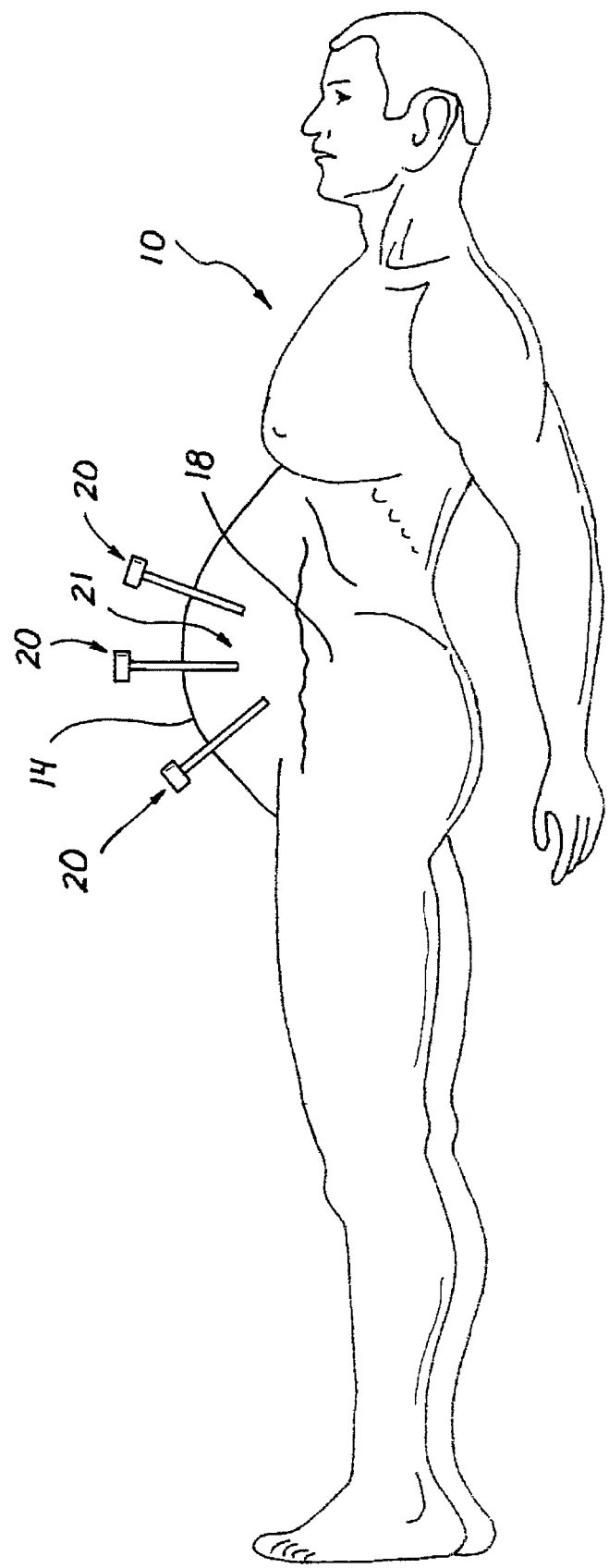
FIG. 3 is a side elevation view of the patient with an inflated abdominal cavity.

It is for this reason that placement of the trocars 20 is commonly preceded with inflation of the abdominal region in order to create an abdominal cavity 21. This initial step of inflating or insufflating the abdominal region 16 produces space between the abdominal wall 14 and the internal organs 18 as best illustrated in FIG. 3. With this separation or space, placement of the trocars 20 is facilitated with a reduced threat to the internal organs 18. Formation of the abdominal cavity 21 also increases the size of the operative environment and enhance visualization of the operative procedure.

Creation of the abdominal cavity 21 has typically been accomplished using an insufflation or Veress needle 23 as illustrated in FIG. 1. This needle 23 has included an elongate cannula 25 having a distal end 27 and a proximal end 30. At the distal end 27, the cannula has been provided with a sharp distal tip 31 of comparative interest to the present invention. At the proximal end 30, the cannula 25 has been coupled through a housing 32 to a connector 34. A source of gas under pressure 36 has been coupled to the connector 34 to provide the insufflation gas through the cannula 25.

Figure 4:
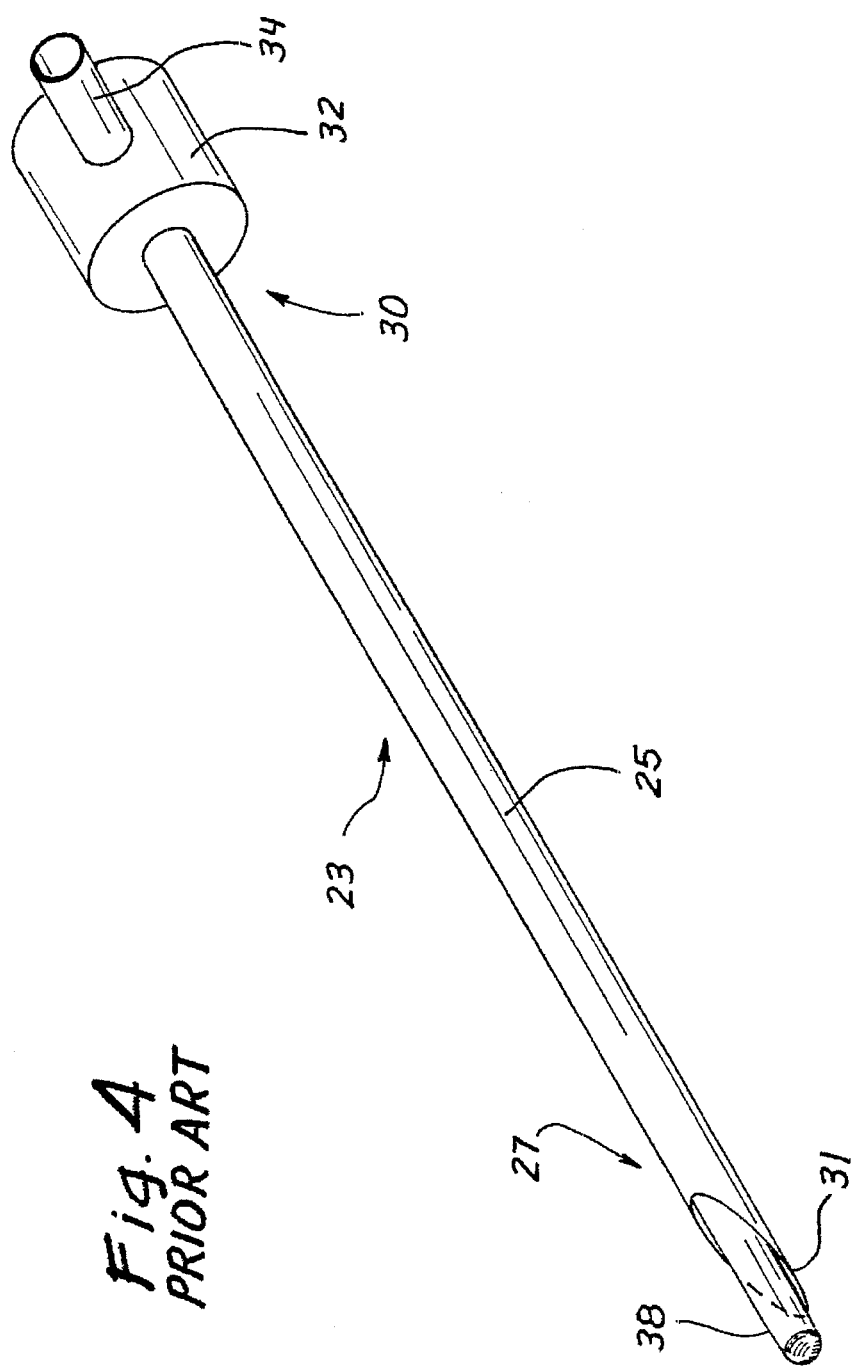
FIG. 4 is a perspective view of an insufflation needle of the prior art.

It is of particular importance to note that when the Veress needle 23 of the past is initially forced through the abdominal wall 14, there is no abdominal cavity 21. As a consequence, the internal organs 18 are not spaced from the abdominal wall 14, but are disposed closely adjacent to the abdominal wall 14 as illustrated in FIG. 1. In order to avoid puncture of these internal organs 18 by the sharp distal tip 31 of the insufflation needle 23, a spring actuated safety member 38 has been provided as best illustrated in the enlarged view of FIG. 4.

Note that the present procedure for placement of the Veress needle has generally required that the needle be inserted perpendicular to the abdominal wall 14. This has produced a perpendicular exit angle with an inner surface 39 of the abdominal wall 14, and most importantly has produced a highly detrimental perpendicular relationship between the Veress needle 23 and the interior organs 18.

Figure 5:
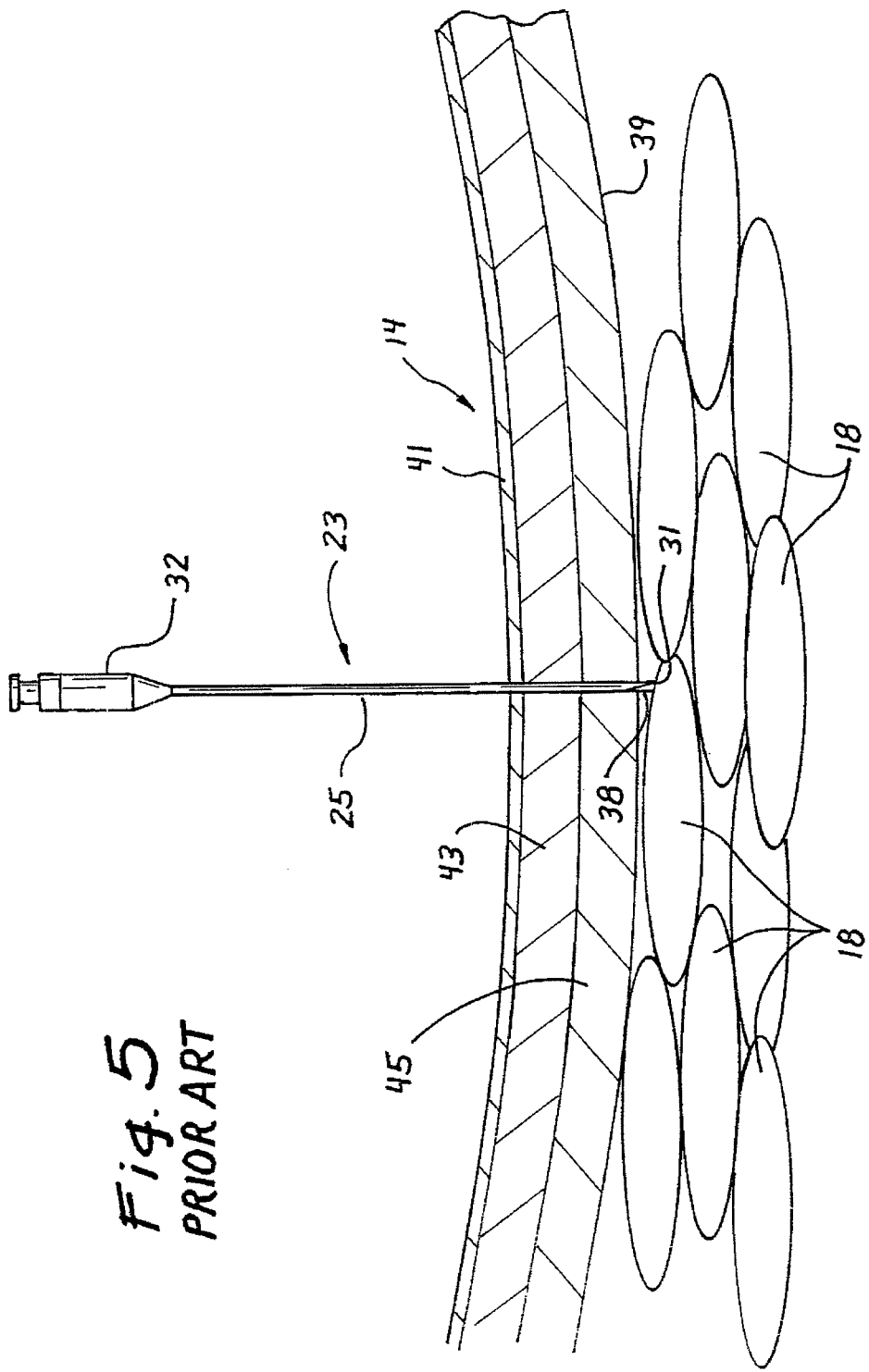
FIG. 5 illustrates an initial step in an insertion method associated with the insufflation needles of the prior art.

In order to fully understand this critical moment when an access device first emerges from the abdominal walls, reference is now made to FIG. 5 which shows a greatly enlarged view of the abdominal wall 14 with the internal organs 18 in close proximity. At the particular time illustrated, the Veress needle 23 has been forced through the abdominal wall 14 and the sharp distal tip 31 has just become exposed at an inner surface 39 of the abdominal wall 14. With the intent of avoiding any damage to the internal organs 18 by the sharp distal tip 31, the safety member 38 has been deployed in this limited time and narrow space to shield the distal tip 31.

The mechanical requirements of this safety member deployment have limited the timeliness of this protection with consequent damage to the internal organs 18. While the safety member 38 reduces the probability of organ damage, the severity of this adverse occurrence remains significant. Furthermore, if a blood vessel is cut or an organ penetrated, the insufflation gas pressure will tend to inhibit any leakage that might alert one to the damage. Under these circumstances, the procedure can be fully completed with the resulting damage becoming apparent only after the insufflation pressure has been relieved and the operative site has been closed. This threatened exposure of the interior organs 18 can also be seen in the wider view of FIG. 6.

Figure 6:
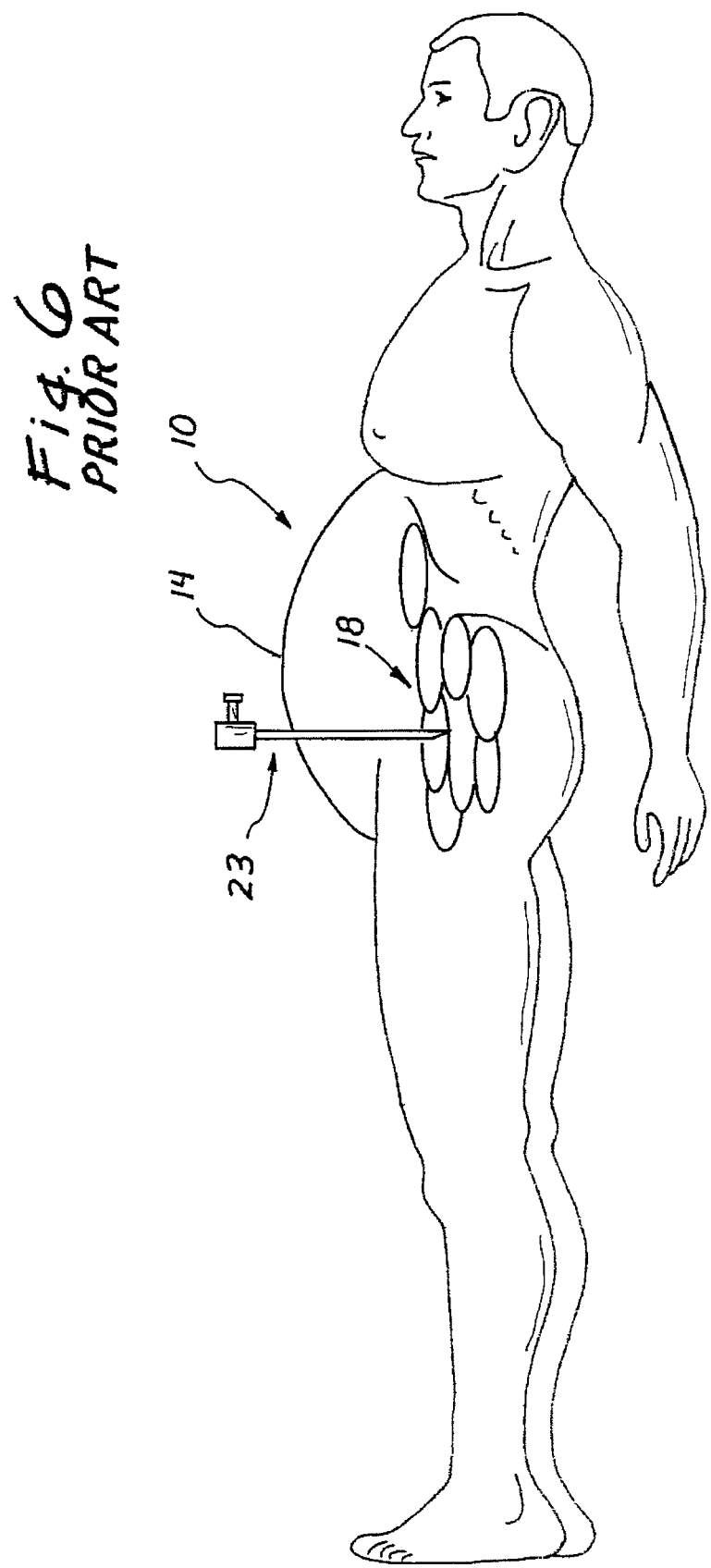
FIG. 6 illustrates an undesirable puncture of internal organs which can result when using the insufflation needles of the prior art.

It can be seen from FIGS. 5 and 6 that great care has been required during insertion of the Veress needle 23 in order to avoid damage to the adjacent internal organs 18. The needle 23 is commonly inserted through the abdominal wall 14 by pushing forward or distally. The forward motion must be carefully controlled to avoid overshooting the abdominal wall 14 and inadvertently penetrating one of the internal organs 18 before the safety member 38 can respond and move forward to shield the sharp tip 31. This has required that the spring force be carefully balanced between that which is required to penetrate the abdominal wall 14 and that which is required to prevent penetration of the internal organs 18.

As illustrated in FIG. 5, the abdominal wall 14 consists of skin 41, layers of muscle 43 and a layer of connective tissue 45. In addition, there is a final, internal membrane 47 referred to as the peritoneum. This membrane 47, which forms the inner surface 39 of the abdominal wall 14, may be very thin and delicate or it may be very tough. In the latter case, the safety member 38 associated with the distal end 27 of the Veress needle 23 may be unable to respond in sufficient time to be effective, particularly if the peritoneum exerts an elastic load as the needle 23 is urged forward. In short, an abrupt rupture of the peritoneum 47 may allow a sharp, unshielded tip to penetrate the internal organs 18 before the safety member 38 can respond.

Referring to FIG. 7, a preferred embodiment of an insufflation device 101 of the present invention is shown in the configuration of a coil 102 formed of a spiraled length of hollow tubing 103. The coil 103 has a diameter 104, and an axis 105 extending between a proximal end 107 and a distal end 110.

At the distal end 110, a distal tip 111 can be rounded or blunted to ensure that there are no sharp edges to cut or tear body tissue. The distal end 110 may have at least one side port 112 that permits gas to escape from the lumen of the tubing 103. The proximal end 107 of the coil 102 may include a tubular extension 114 terminating in a connector 116 which is adapted to be coupled to the source of gas 36 (FIG. 1). The coil 102 can be formed with individual convolutions 118 which are spaced to provide maximum engagement with the body tissue while avoiding overcompression and necrosis of the tissue.

Figure 8:
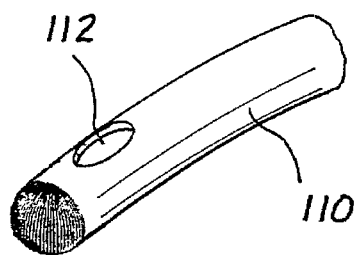
FIG. 8 is an enlarged perspective view of one embodiment of a distal end portion of the insufflation device illustrated in FIG. 7.

With reference to FIG. 8, it will be appreciated that the distal end 110 of the coiled insufflation device 101 can be substantially or completely closed and formed with a hemispherical distal tip 111 providing a smooth transition to the coiled tubing 103. The side port 112 is preferably sized and configured to deliver maximum gas flow from the coiled tubing 103 to the abdominal cavity 21.

Figure 9:
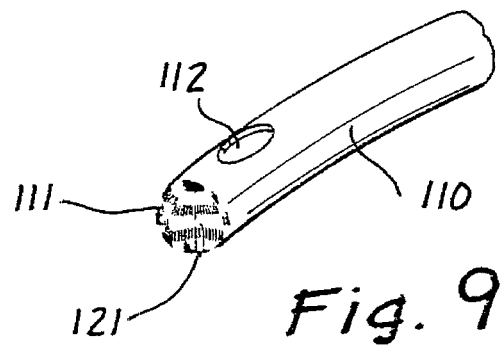
FIG. 9 is an enlarged perspective view of the distal end portion of an alternate embodiment of the insufflation device.

In an alternate embodiment illustrated in FIG. 9, the distal tip 111 is formed from a material that is optically clear. This allows use of an optical viewing device 121, such as an endoscope, angioscope or the like. In such an embodiment, the optical viewing device 121 could be disposed in the lumen of the coiled tubing 103 and subsequently advanced to the distal end 110 for visually monitoring insertion of the insufflation device 101.

It will be noted by comparison, that in the past, insertion of the Veress needle 23 was a blind procedure which presented the greatest threat to the internal organs 18 (FIG. 2). Only after the Veress needle 23 had created the inflated abdominal cavity 21 and the first trocar 20 was placed, could an endoscope be inserted to facilitate visualization during insertion of subsequent trocars. With the present device, this visualization is available to provide for safe placement of the access device which initially crosses the abdominal wall 14.

Figure 10:
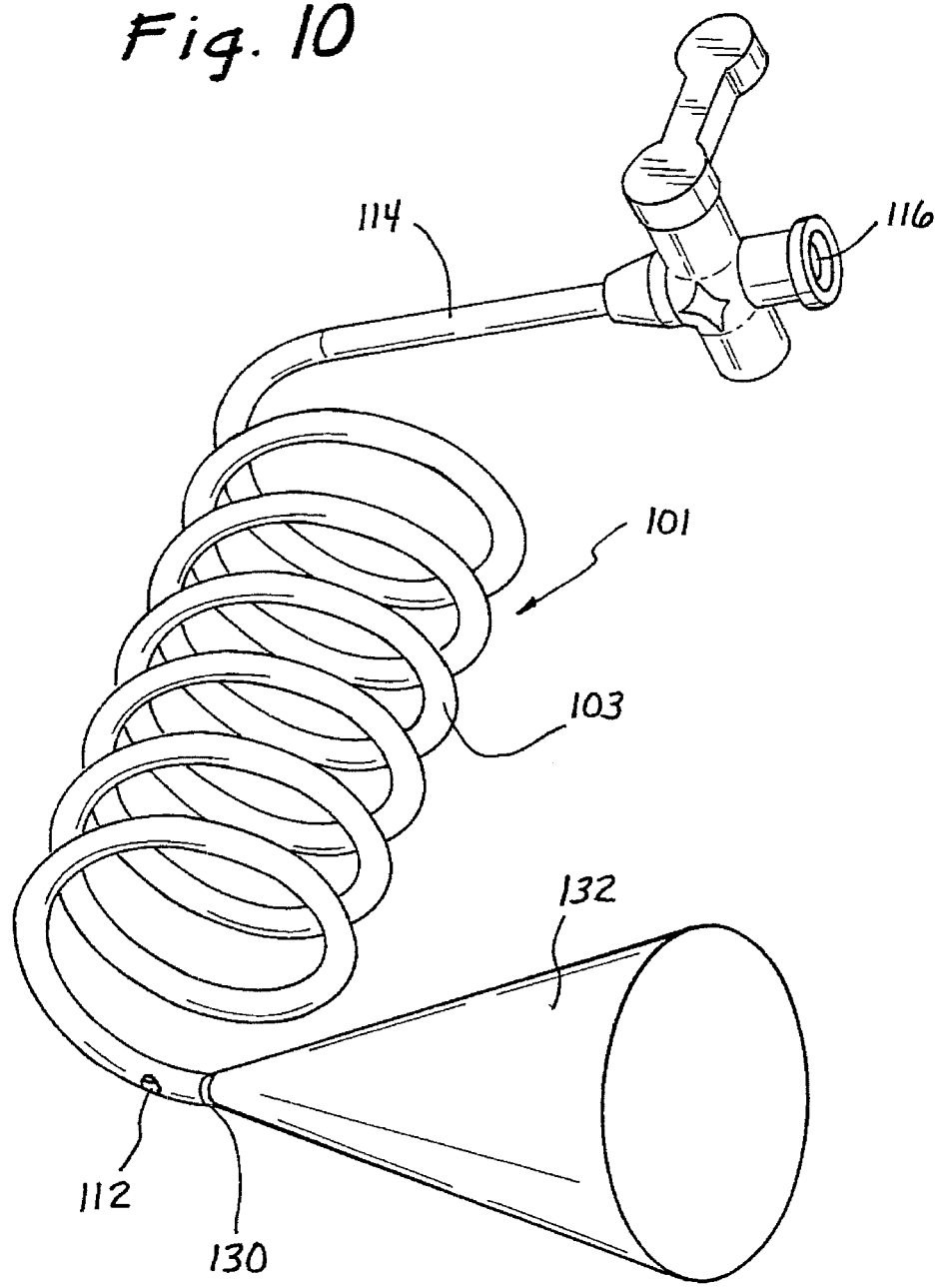
FIG. 10 is a perspective view of an alternate embodiment of the device including a distal tip emitting visible light.

In another embodiment illustrated in FIG. 10, the optical viewing device 121 may include an illumination device or light 130 within the lumen of the coiled tubing 103. In this case, the light 130 will produce an illuminated area 132 that is viewable from outside the body of the patient 10. This form of viewing, which is commonly referred to as transillumination, provides a clear indication as to the position of the distal end 110 when it has reached a preferred location. The indication may be some change in the emission characteristics of the light 130, or may result from diffusion of the omitted light in a manner that indicates proper placement.

Figure 11:
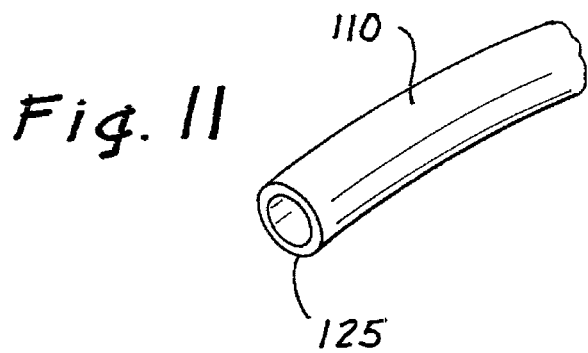
FIG. 11 is an enlarged perspective view of the distal end portion in another embodiment of the insufflation device.
Figure 12:
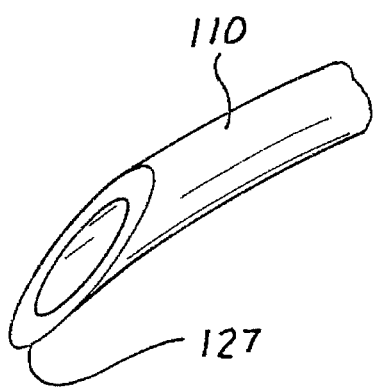
FIG. 12 is an enlarged perspective view of the distal end portion in a further embodiment of the insufflation device.

Referring now to FIGS. 11 and 12, the distal tip 111 of the coiled tubing 103 may present an end condition that is not rounded. For instance, the coil tubing 103 may terminate in a straight perpendicular surface 125 as illustrated in FIG. 11. In this case, the lumen of the tubing 103 would be unobstructed.

In the embodiment of FIG. 12, the distal end 110 is provided with a sharp, pointed tip 127. Although the preferred embodiment of the present invention comprises a blunt or rounded tip 111, the sharp tip 127 of the FIG. 12 embodiment still offers the significant advantage associated with the reduced entry and exit angles provided by the coil construction.

Figure 13:
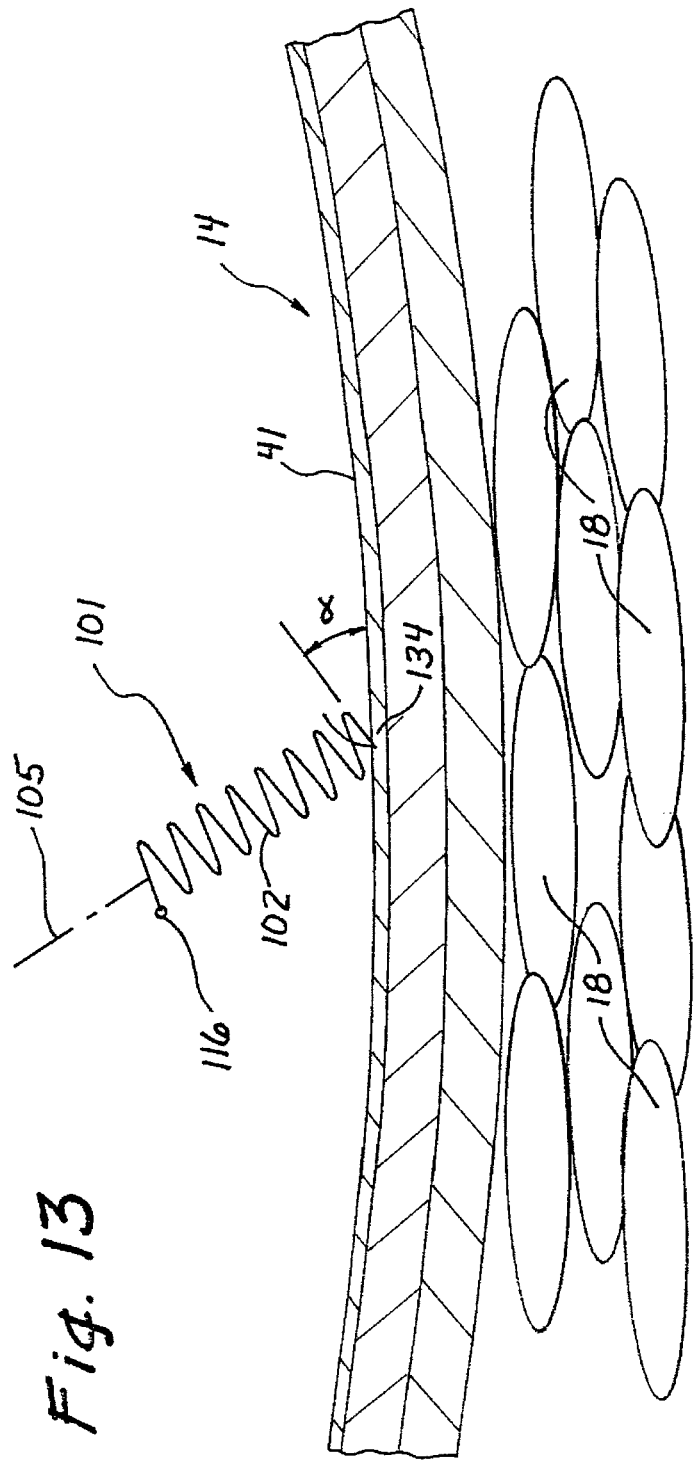
FIG. 13 is an enlarged cross-section view of the abdominal wall showing an initial step in a preferred method for insertion of the device.
Figure 14:
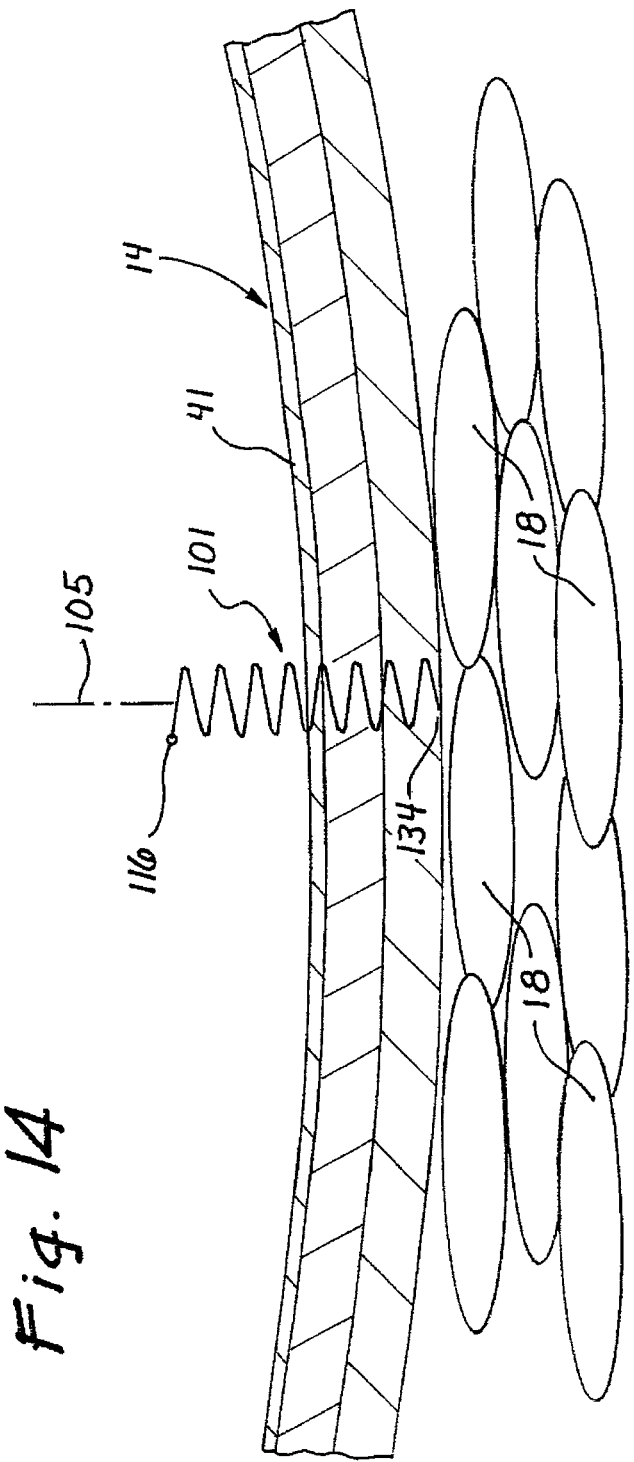
FIG. 14 is an enlarged cross-sectional view of the abdominal wall showing a continuing step in a preferred method for insertion.
Figure 15:
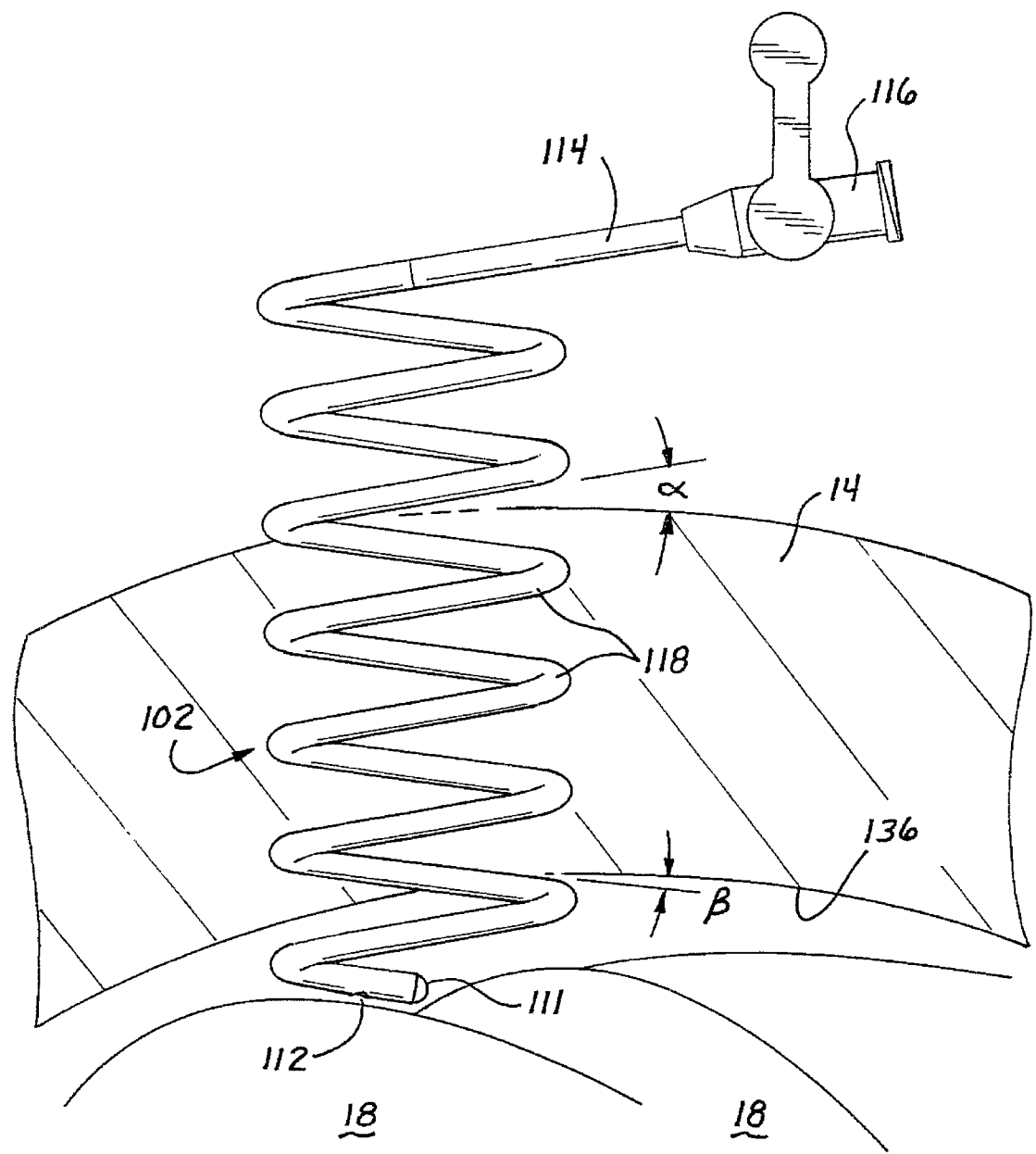
FIG. 15 is a close-up view of the abdominal wall illustrating a further step in the insertion method as the distal end emerges in close proximity to the internal organs of the patient.

These entry and exit angles can be further appreciated with reference to FIGS. 13, 14, and 15 which show progressive positions of the insufflation device 101 as it is maneuvered through the abdominal wall 14. In FIG. 13, a nick 134 has been made in the skin 41 of the wall 14. By placing the axis 105 of the coil 102 at an angle to the abdominal wall 14, the entry angle of the distal tip 121 can be increased to facilitate passage through the nick 134. In FIG. 13, this entry angle is designated by the Greek letter α. After the nick 134 has been penetrated, the coil 102 is preferably oriented so that its axis 105 is substantially perpendicular to the abdominal wall 14 as illustrated in FIG. 14. This greatly reduces the entry angle α as the distal tip 121 passes through the layer of muscle 43 and associated connective tissue 45 (FIG. 5) which comprise the abdominal wall 14.

Continued penetration of the coiled tubing 103 through the abdominal wall 14 is illustrated in FIG. 14. As the coil 102 passes through the abdominal wall 14, as illustrated in the enlarged view of FIG. 15, the distal tip and the following convolutions 118 exit the wall 14 at an exit angle designated by the Greek letter β in FIG. 15.

It is this exit angle β which is of particular importance to the present invention. Although this angle is measured with respect to an inner surface 136 of the abdominal wall 14, it can be appreciated that the internal organs 18 are also in contact with, or generally parallel to this inner surface 136. Accordingly, the exit angle β is also the angle which the distal tip 121 presents to the internal organs 18. When this angle is generally perpendicular, as in the past (see FIG. 6), the probability of organ penetration is great. However, when this exit angle β is reduced to a very small acute angle, the distal tip 111 tends to slide along the surface of the internal organs 18, particularly if the distal tip 111 has a blunt configuration as first discussed with reference to FIG. 8.

Figure 16:
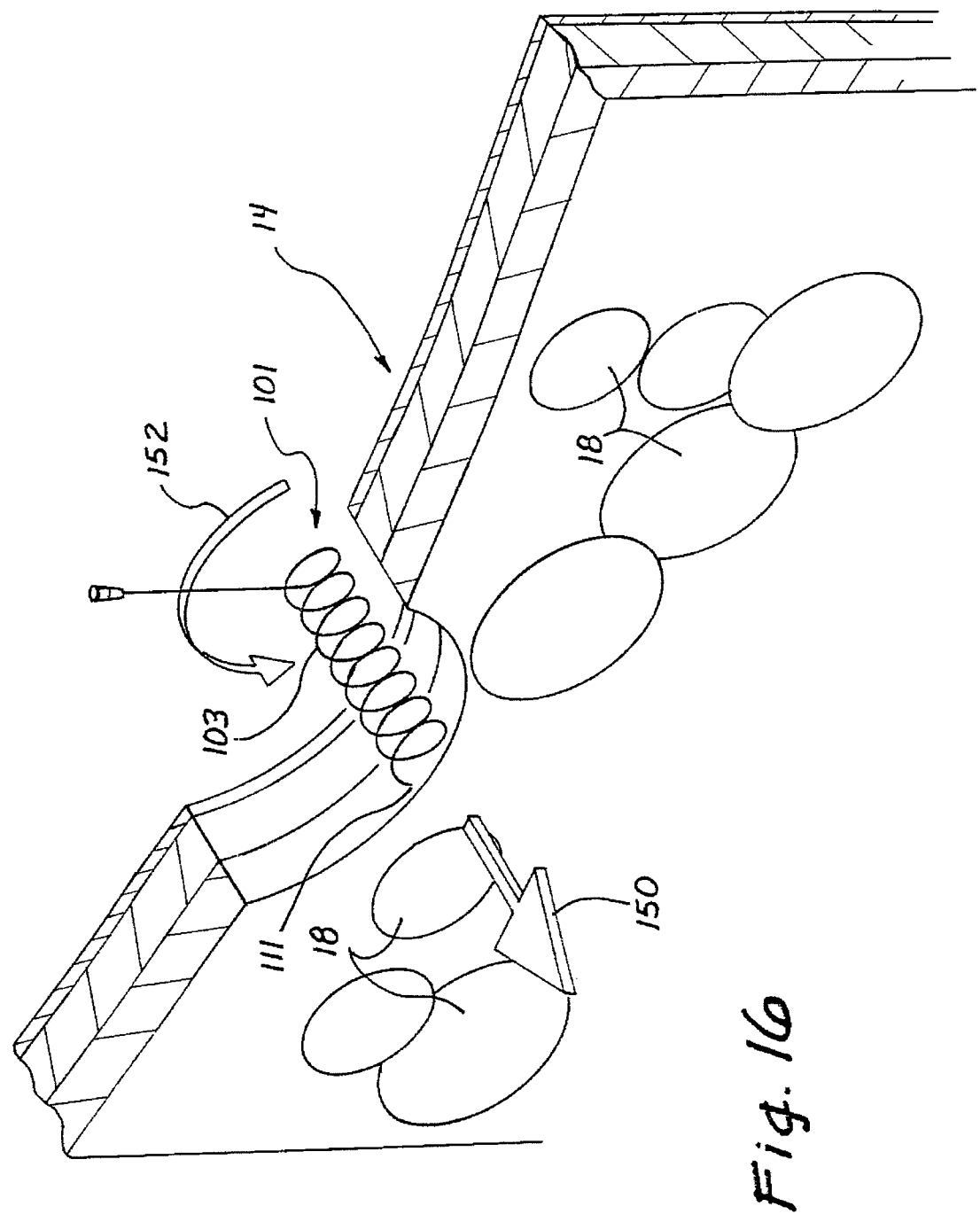
FIG. 16 is a schematic perspective view of the device within the abdominal wall.

In FIG. 16, the coiled device 101 of the present invention is illustrated schematically so that one can appreciate the forces associated with placement of the device 101 through the body wall 14. In the past, the straight Veress needle 23 (FIG. 1) would be placed using a force applied in the same direction as that desired for movement of the device 101, specifically a forward force applied in the direction represented by an arrow 150. Note that the insufflation device 101 of the present embodiment moves in the desired forward direction 150, but does so only in response to a rotational force represented by an arrow 152. The forward direction of movement illustrated by the arrow 150, may even be realized while the coiled tubing 103 is pulled backwardly by a force opposite to the forward direction of arrow 150. In other words, once the distal tip 111 is adequately engaged within the abdominal wall 14, FIG. 13, preferably within a small skin incision or nick 134 (FIG. 13), the entire device 101 may be held in traction rather than pushed to provide the desired forward motion. The coiled tubing 103 acts as a "corkscrew" and propels or advances itself in the forward direction 150, but only in response to rotational motion shown by arrow 152. This tractional rotation of the coiled tubing 103 tends to provide a safety margin as the body wall 14 is pulled or drawn away from the internal organs 18.

With further reference to FIG. 7, it can be seen that the present invention may comprise larger than ordinary tubing 103 since the placement force is not perpendicular to the abdominal wall 14 and internal organs 18. In fact, the placement force, as shown by arrow 152, is rotational and incremental rather than direct and uncontrollable. In addition, the slow and deliberate advancement of the blunt distal end 110 gradually parts tissue, such as the skin 41, muscle 43, and connective tissue 45 in a more natural manner than with the straight, cutting penetration of the past. The blunt distal end 110 tends to wind its way through body tissue seeking weak, less dense or fatty tissue, and avoiding included blood vessels, and muscle that is normally more vascular than fatty tissue.

Figure 17:
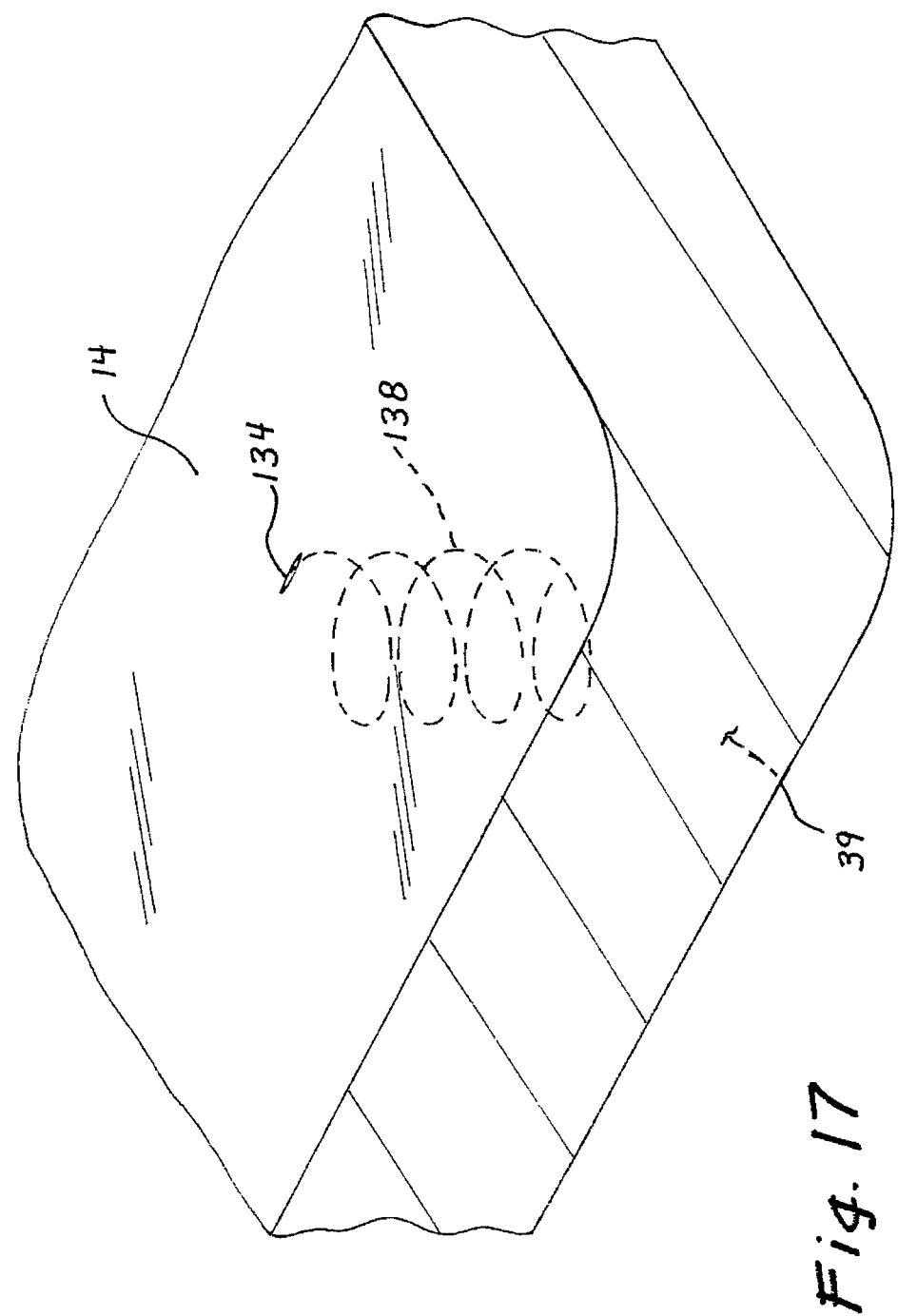
FIG. 17 is a perspective view of a wound site after removal of the device.

An insertion site 21 associated with the present invention is shown in FIG. 17 at a time when the device 101 has been removed, and the tissue, previously separated by the procedure, has generally returned to its original condition. Since little or no cutting has occurred, there is minimal bleeding and no potential for herniation of the site. A track 154 through which the device 101 passes as it is rotated through the tissue, has the same length and convoluted nature as the device 101 itself. With respect to the track 138, its length, convoluted nature and general lack of cut tissue provides improved healing even though the diameter size of the insufflation device 101 may have been as much as two or three times that of existing insufflation needles.

With further reference to this enlarged diameter, it will be noted that the insufflation device 101 can provide a gas flow significantly greater than existing insufflation needles. But even if the diameter or gauge size of the present insufflation device 101 is the same as that of the prior art, its gas flow will be significantly greater primarily due to the lack of obstruction in the lumen of the tubing 103.

Many of the advantages associated with the coiled insufflation device 101 can be further appreciated in combination with a trocar, such as the trocar 20 discussed with reference to FIG. 3. In this combination, illustrated in FIG. 18, the trocar 20 is shown to have a valve housing 141, a cannula 143, and a removable obturator 145. The coiled insufflation device 101 is rotatably attached to the trocar 20, for example with an attachment ring 147.

The trocar 20 is preferably disposed inside of and coaxial with the coiled insufflation device 101. With this orientation, the device 101 is free to rotate on its axis around the cannula 143 of the trocar 20. The device 101 will typically be as long as, if not slightly longer than, the cannula 143 so that the distal tip 111 extends at least to the tip of the obturator 145.

Figure 19:
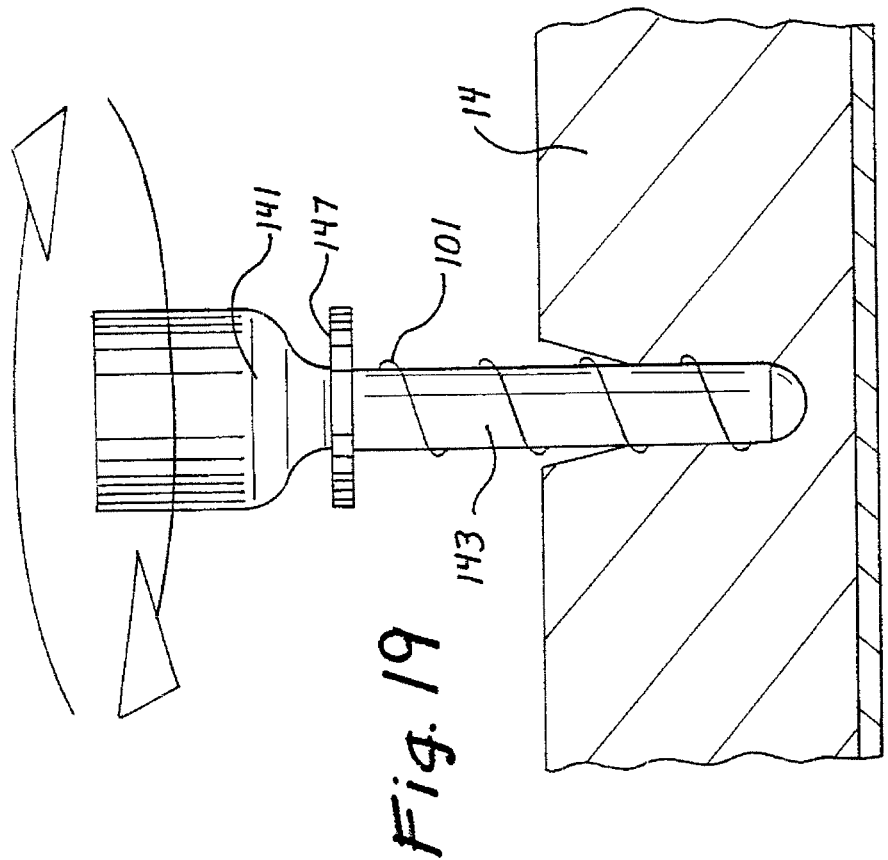
FIG. 19 is a front elevation view showing the combination of FIG. 18 in use to cross the abdominal wall.

Operation of this combination is illustrated in FIG. 19. As the coiled insufflation device 101 is rotated into the abdominal wall 14 of the patient, it advances in the manner previously discussed. Due to its attachment to the trocar 20, this advancement tends to pull the trocar into the abdominal wall 14. One major advantage associated with this combination is that the device 101 provides an outward counter force which resists any tendency of the abdominal wall 14 to tent inwardly due to the forward movement of the trocar 20.

This system would be particularly useful for bariatric patients which have a large quantity of abdominal wall fat. In these patients, often a large amount of leverage must be applied against the trocar to overcome the bulk of abdominal wall fat. This in turn widens the trocar entry wound and makes slippage of the trocar more likely. With the combination of the trocar 20 and insufflation device 101, the surgeon does not have to fight the abdominal wall during insertion and will further benefit from the tremendous retention provided by the insufflation device 101.

A further advantage associated with this combination can be appreciated by noting that trocars are typically placed normal to the surface of the abdominal wall 14 and also normal to the peritoneum. In the past, an inwardly directed force was applied to the trocar 20 to push the trocar 20 through the abdominal wall 14. This force caused the abdominal wall to tent inwardly as the force was directed against succeeding muscular and fat layers of the wall 14. Ultimately, the force was directed against the peritoneum.

With the present combination, the device 101 can be pulled with an outwardly directed force while the trocar 20 is pushed with an inwardly directed force. When the outward force exceeds the inward force, two significant advantages are realized. First, there is no inward tenting: Second, the abdominal wall is elevated creating an abdominal cavity separating the abdominal wall from the internal organs. Creation of this cavity greatly reduces any risk of damage to the organs when wall 14 is finally penetrated by the trocar 20.

Not withstanding these significant features, the device 101 provides a further advantage as it functions to hold the peritoneum against the remainder of the abdominal wall 14. This feature resists any tendency toward peritoneal separation regardless of its cause. For the first time, angular placement of the trocar 20 can be accommodated without a risk of separating the peritoneum from the adjacent layer of the abdominal wall 14. Angular placement will also enable the surgeon to reach lateral internal sites more easily, without forcing the trocar 20 to cant with commensurate stress on the instruments.

Figure 20:
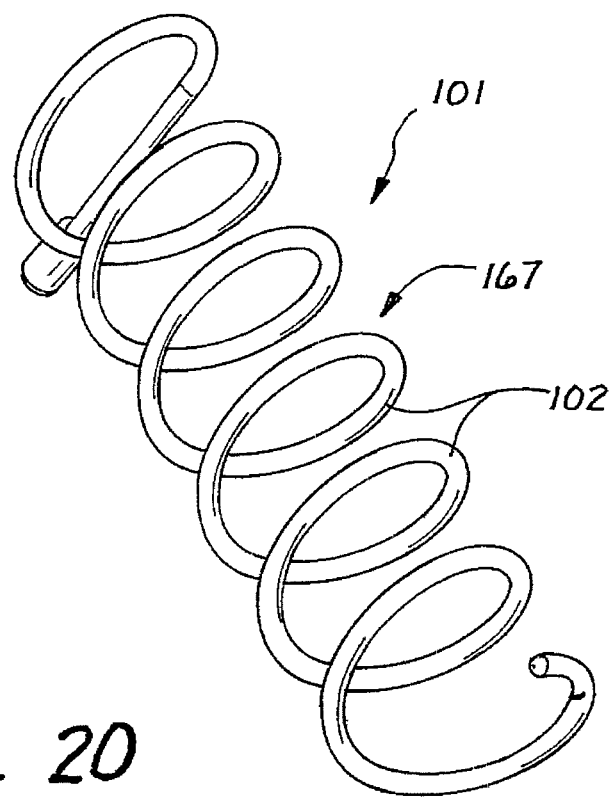
Figure 21:
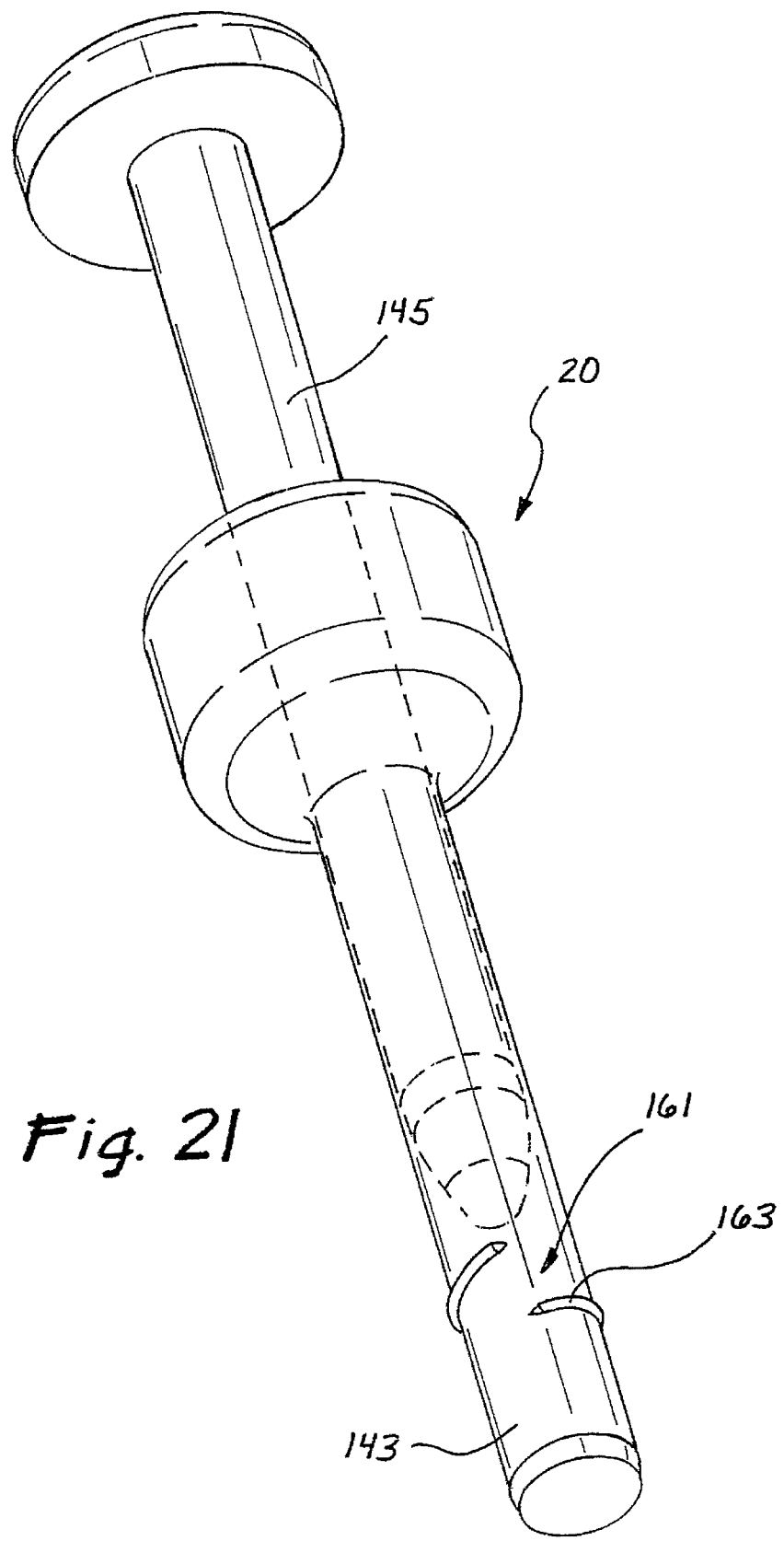

A further embodiment of the invention is illustrated in FIGS. 21-24. This embodiment is similar to that of FIG. 18 in that it includes the insufflation device 101 (FIG. 20), the trocar 20 with cannula 143 (FIG. 21), and the obturator 145 (FIG. 21).

Figure 18:
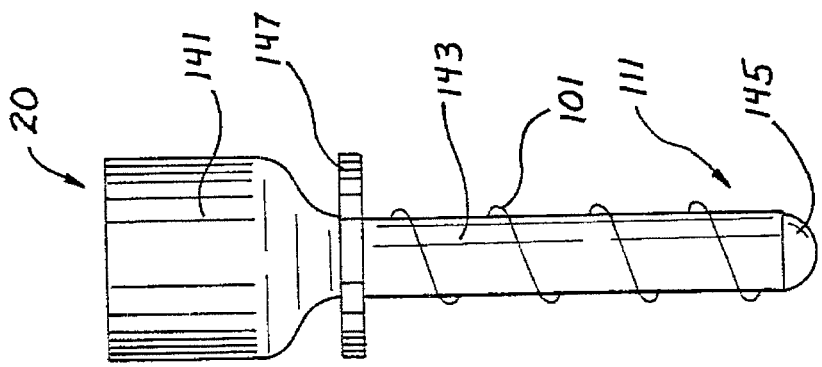
FIG. 18 is a front elevation view of a combination including an insufflation device rotatably attached to a trocar.

However, the embodiment of FIG. 21 differs from that of FIG. 18 in at least two aspects. First, the insufflation device 101 is not attached to the trocar, but rather is separate from the trocar to permit the unique operation discussed in greater detail below. Second, a helix 161 is formed on the outer surface of the cannula 143 of the trocar 20. This helix 161 can be formed with multiple convolutions or preferrably with only a single convolution 163. In this embodiment, the helix 161 functions as an external thread 165 on the trocar 20. Its preferred placement could be anywhere along the cannula 143, or perhaps even on the exposed distal tip of the obturator 145.

Referring now to FIG. 22, it can be seen that the insufflation device 101 can function in this embodiment as an anchor 167 which can be embedded in the abdominal wall 14 in the manner previously discussed. In this operative position, the anchor 167 can function as an insufflation needle; however, in this case the anchor 167 has an additional purpose and that is to provide the helix or coil 102 which can function as an internal thread.

With the anchor 167 functioning as an internal thread and the helix 161 functioning as an external thread, it can be seen that the helix 161 can actually be screwed into the anchor 167 as a bolt would be screwed into a nut. This relationship is best illustrated in FIG. 23.

Once the anchor 167 is screwed into the abdominal wall 14 as illustrated in FIG. 24, the trocar 20 with its external thread or helix 161 can be screwed into the anchor 167 thereby drawing the trocar 20 through the abdominal wall 14. As the helix 161 is screwed into the anchor 167, an internal force is developed between these two structures which moves the trocar 20 forward or distally into the abdominal wall 14. No directional external force is required to produce this forward movement. The user merely rotates the trocar 20 as shown by the arrows 169, to produce the internal force that draws the trocar 20 into the abdominal wall 14.

The system and method associated with this embodiment is particularly beneficial when the trocar 20 is to be inserted at a non-perpendicular angle to the abdominal wall 14. For example, in FIG. 25, the trocar 20 is to be inserted at an angle to the abdominal wall 14. With trocars of the past, this would ultimately bring the distal trip of the obturator into an angular relationship with the peritoneum 171 of the abdominal wall 14. Since the peritoneum 171 forms a relatively strong inner surface of the wall 14, an angular relationship with the trocars of the past has tended to resist penetration of the peritoneum 171 and ultimately separated the peritoneum 171 from the remainder of the wall 14.

Figure 25:
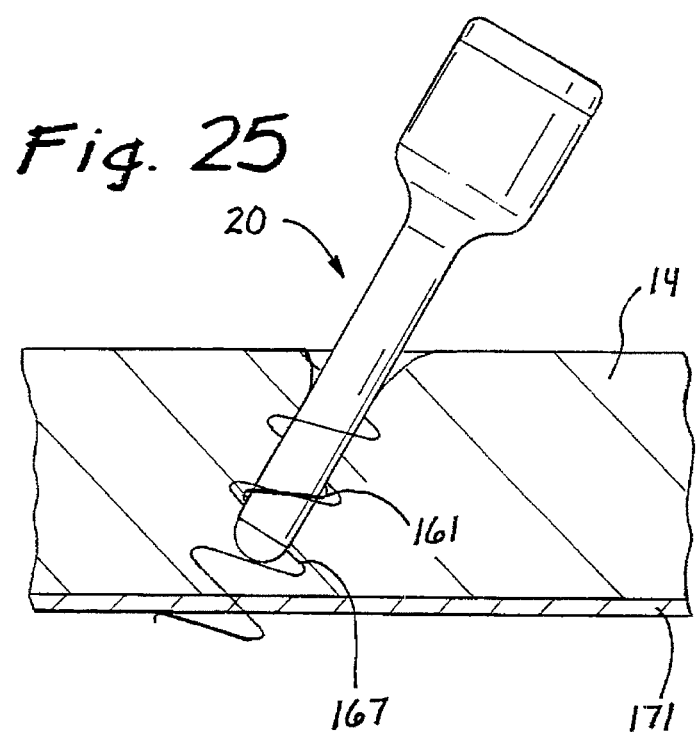
Figure 26:
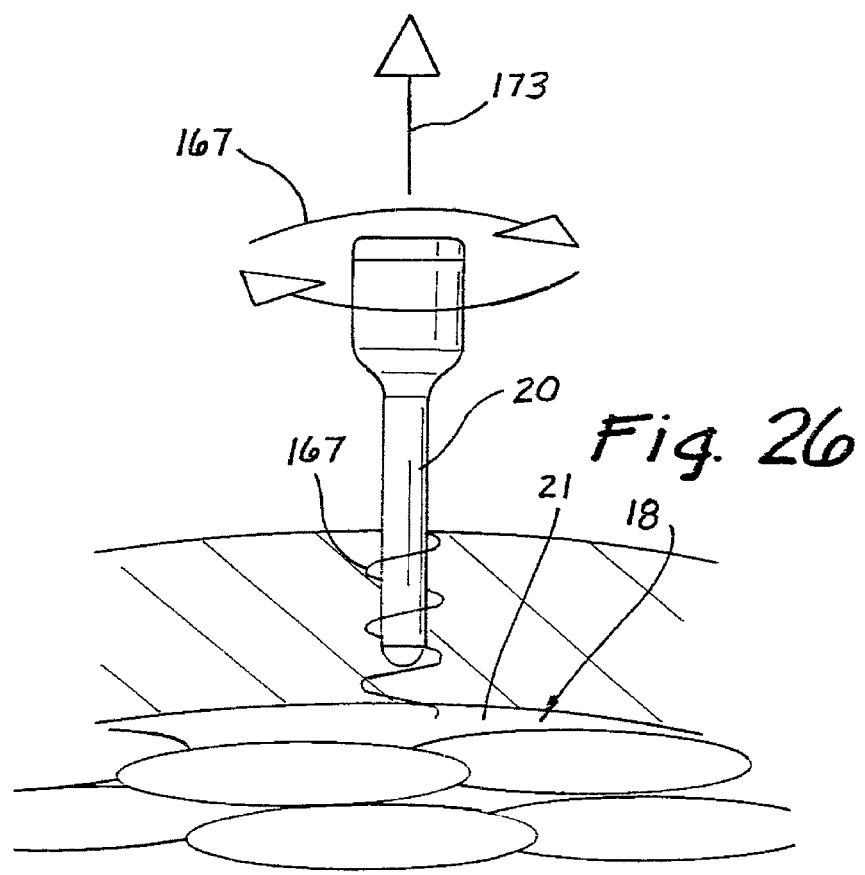

With the present embodiment, the anchor 167 is initially placed at the preferred angle, as illustrated in FIG. 25. Then the trocar 20 is merely threaded along the axis of the anchor 167. In this case, the anchor 167 defines the pathway through the peritoneum 171 and provides a continuous axial force which draws the trocar 20 along the axis of the anchor 167. In this manner, an angular placement of the trocar 20 can be easily achieved without substantial risk of peritoneal separation.

In this embodiment, the anchor 167 can function as an insufflation needle as discussed with reference to previous embodiments. However, certainly one of its primary functions is to helically receive the trocar 20 even while it is being inserted. Once the trocar 20 engages the anchor 167, a rearward or proximate force can be applied to the trocar 20 to elevate the abdominal wall 14 and thereby create the abdominal cavity 21. This external force would typically be applied along the arrow 173 as illustrated in FIG. 24.

It is now interesting to contemplate the external forces applied by the user, in combination with the internal forces developed between the trocar 20 and anchor 167. In operation, the anchor 167 is initially inserted into the abdominal wall 14 in the manner previously discussed. Then the user moves the cannula 143 of the trocar 20 along the axis of the anchor 167 until the external thread or helix 161 engages the internal thread or coil 102 of the anchor 167. The user can then merely turn the trocar in the direction of the arrows 167 to provide an engagement between the helix 161 and coil 102. Once this engagement is achieved, the user can pull the trocar 20 proximally along the arrow 173 to elevate the abdominal wall 14 and produce the abdominal cavity 21. Continued turning of the trocar 20 will produce the internal force between the helix 161 and coil 102 which draws the trocar 20 distally into the elevated abdominal wall 14. When the peritoneum 171 is penetrated, the distal tip of the obturator 145 moves into the abdominal cavity 121 with a substantially reduced risk to the internal organs 18.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

The invention claimed is:

1. A system for providing access across a body wall, the system comprising:
   a length of tubing having a proximal end, a distal end and a tubing lumen having a proximal opening and a distal opening; the overall length of the tubing defining a longitudinal axis and the tubing lumen defining a lumen axis;
   a clear distal tip connected to and closing the distal opening of the tubing; the clear distal tip being adapted to penetrate tissue and provide optical viewing through the distal tip;
   a trocar comprising an elongated shaft having a proximal end and a distal end defining a longitudinal axis and a lumen; the trocar being disposed inside of the tubing such that the longitudinal axis of the tubing is co-axial with the longitudinal axis of the trocar;
   wherein the lumen axis at the distal end of the tubing is angled with respect to the longitudinal axis such that optical viewing through the clear distal tip is generally along the lumen axis and angled with respect to the longitudinal axis; and
   wherein the tubing is coiled around the outside of the trocar.

2. The system of claim 1 further including an optical element disposed inside the lumen of the tubing and located at the distal end for visually monitoring through the clear distal tip at an angle to the longitudinal axis.

3. The system of claim 2 wherein the optical element includes an illumination device.

4. The system of claim 1
wherein the proximal opening is connected to a source of fluid under pressure and the distal end includes at least one port formed in the tubing adjacent to the distal opening; the at least one port being adapted to expel the fluid under pressure.

5. The system of claim 1 wherein the distal tip is blunt.

6. The system of claim 1
wherein the distal end includes at least one port adjacent to the distal opening.

7. The system of claim 1 further including
a removable obturator inside the lumen of the trocar.

8. The system of claim 7 wherein the distal end of the tubing extends slightly beyond the obturator and movement of the tubing is accompanied by movement of the obturator such that the penetrating distal end of the tubing leads the blunt distal end of the obturator through the body wall.

9. A system for providing access across a body wall, the system comprising:
a trocar comprising a cannula having a lumen;
a length of tubing having a proximal end and a distal end adapted to penetrate tissue; the length of the tubing defining a longitudinal axis and coaxially surrounding the cannula;
an obturator comprising an elongated shaft with a blunt distal end and longitudinal axis; the obturator being coaxially disposed within the cannula;
wherein the distal end of the tubing extends slightly beyond the obturator and movement of the tubing is accompanied by movement of the obturator such that the penetrating distal end of the tubing leads the blunt distal end of the obturator through the body wall; and
wherein the tubing is configured in the shape of a coil.

10. The system of claim 9 wherein movement of the tubing pulls the obturator through the body wall.

11. The system of claim 9 wherein the tubing is rotatable relative to the trocar.

12. The system of claim 9 wherein the tubing is connected to the trocar such that longitudinal movement of the tubing is fixed and the tubing is rotatable relative to the trocar.

13. The system of claim 9 wherein the distal end of the tubing has a sharp pointed tip.

14. The system of claim 9 wherein the distal tip has a distal end that is angled with respect to the lumen axis such that the most distal point of the distal end is offset from the lumen axis.

15. The system of claim 9 wherein the distal tip is curved.

16. A system for providing access across a body wall, the system comprising:
a trocar comprising a cannula having a lumen;
a length of tubing having a proximal end and a distal end adapted to penetrate tissue; the length of the tubing defining a longitudinal axis and coaxially surrounding the cannula;
an obturator comprising an elongated shaft with a blunt distal end and longitudinal axis; the obturator being coaxially disposed within the cannula;
wherein the distal end of the tubing extends slightly beyond the obturator and movement of the tubing is accompanied by movement of the obturator such that the penetrating distal end of the tubing leads the blunt distal end of the obturator through the body wall; and
wherein the tubing is configured in the shape of a coil and rotational movement of the tubing pulls the obturator through the body wall.

* * * * *